United States Patent [19]

Koppenhagen et al.

[11] 4,407,947

[45] Oct. 4, 1983

[54] PROCESS FOR OBTAINING METAL-FREE CORRINOIDS

[75] Inventors: Volker Koppenhagen, Braunschweig-Stöckheim, Fed. Rep. of Germany; Gerhard Schlingmann, Berkeley, Calif.; Bernd Dresow, Brunswick; Ludwig Bischoff, Braunschweig-Geitelde; Rosemarie Penkert, Brunswick; Eicke Siefert, Göttingen, all of Fed. Rep. of Germany

[73] Assignee: Gesellschaft fur Biotechnologische Forschung mbH (GBF), Braunschweig-Stöckheim, Fed. Rep. of Germany

[21] Appl. No.: 302,022

[22] Filed: Sep. 14, 1981

Related U.S. Application Data

[63] Continuation of Ser. No. 127,365, Mar. 4, 1980, abandoned.

[30] Foreign Application Priority Data

Mar. 6, 1979 [DE] Fed. Rep. of Germany ....... 2908769

[51] Int. Cl.³ .................... C12P 19/28; C12P 19/42
[52] U.S. Cl. .................................. 435/85; 435/86
[58] Field of Search .................... 435/119, 86, 85

[56] References Cited

U.S. PATENT DOCUMENTS 3,846,237 11/1974 Toohey .................... 435/86

Primary Examiner—Alvin E. Tanenholtz
Attorney, Agent, or Firm—Hammond & Littell, Weissenberger and Muserlian

[57] ABSTRACT

A process for obtaining metal-free corrinoids consisting of inoculating a culture media free of added compounds of metals of the VIIIth group of the Periodic Table with a parent strain of Rhodopseudomonas, cultivating under illumination, repeating the steps of inoculating and cultivating employing said culture media and said illumination employing a part of the sequential culture from the preceding stage as an inoculum in each subsequent state, for a series of several pre-production culture stages, inoculating said culture media with the preceding sequential culture for the last time, cultivating under illumination, separating the microorganism from the culture media of the production culture stage and isolating metal-free corrinoids from the culture media of the production culture stage.

26 Claims, No Drawings

PROCESS FOR OBTAINING METAL-FREE CORRINOIDS

This is a continuation of Ser. No. 127,365, filed Mar. 4, 1980 and now abandoned.

German Offenlegungsschrift No. 1 642 749 has already claimed processes for obtaining metal-free corrinoids comprising cultivating phototrophic organisms, such as *Rhodopseudomonas pallustris,* under illumination and separating the micro-organisms from the culture medium. In these known processes the metal-free corrinoids are subsequently isolated from the micro-organisms which have been separated off. However, in these known processes it has still not been possible to obtain a satisfactory yield. The largest quantities that it has previously been possible to isolate from cells of phototrophic micro-organisms are for chromatium, and amount to approximately 0.1 mg/moist bacterial mass per liter. However, because the extinction coefficients have since been more accurately determined, this value has to be corrected to 0.06 mg/moist bacterial mass per liter.

Evidently because of the light-sensitivity of the metal-free corrinoids specified in the mentioned German Offenlegungsschrift, the possibility of obtaining this class of substance from the culture medium of such phototrophic micro-organisms has so far not been investigated. It must therefore be regarded as surprising that according to the invention there is a process available for obtaining metal-free corrinoids in which a strain of Rhodopseudomonas is cultivated under illumination and the micro-organism is separated from the culture medium, the process being distinguished by the fact that the metal-free corrinoids formed are isolated from the culture medium in a manner known per se.

The expert is able to isolate, identify and cultivate Rhodopseudomonas strains at any time from natural sources; in this connection reference may be made to the following works:

Weaver et al., Arch. Mikrobiol., 105 (1975) 215;

Biebl & Drews, ZB1. Bakteriol. Parasitenk. Infektionskr. Hygiene, Abt. 2, 123 (1969) 452;

Pfennig & Trüper in "Bergey's Manual of Determinative Bacteriology", 8th edition, Baltimore, (1974) 25–65;

Dresow, Dissertation, Braunschweig 1978; and

German Offenlegungsschrift No. 1 642 749.

The expert is also conversant with the isolation of metal-free corrinoids from liquid media; compare, for example:

Koppenhagen & Pfiffner, J. Biol. Chem., 245 (1970) 5865–5867;

Koppenhagen & Pfiffner, J. Biol. Chem., 246 (1971) 3075–3077;

Koppenhagen et al., J. Biol. Chem., 248 (1973) 7999–8002;

Dresow, Dissertation, Braunschweig 1978; and

German Offenlegungsschrift No. 1 642 749.

Examples of Rhodopseudomonas strains are *Rhodopseudomonas sphaeroides, capsulata* and *pallustris.* The following details can be given for the deposition of the strains specifically named hereinafter:

| Strain | Place of deposit | Deposit number |
|---|---|---|
| Rhodopseudomonas sphaeroides | DSM Göttingen | 158 |
| Rhodopseudomonas capsulata | DSM Göttingen | 155 |

In obtaining metal-free corrinoids by the process according to the invention it is important to work with as small as possible a concentration of Fe in the production medium and with Co substantially excluded. Thus, one embodiment of the process provides for a specific depletion of Fe and Co; in this case, starting from a culture of the parent strain (starting culture), in succession several (for example 4 to 9) precultures (sequential cultures) and finally the production culture (last sequential culture) are prepared, in each case by inoculating a nutrient medium, to which in particular no compound of metals of the VIIIth group of the Periodic Table has been added, with a part (for example 5 to 25%, and especially 10%) of the preceding culture. In a specific embodiment of the process, the sequential culture in which an extra-cellular minimum concentration of metal-free corrinoids of 0.1 mg/liter, preferably 0.5 mg/liter and especially 1 mg/liter, is obtainable is selected as the final production culture or as the inoculation culture for the production culture.

On the other hand, the starting culture which has been used to initiate this gradual depletion of Fe and Co ions can be kept as the parent culture in a nutrient medium to which ions or compounds of metals belonging to the VIIIth group of the Periodic Table (for example iron ions) have also been added, such as the medium described by Pfennig in Arch. Mikrobiol., 100(1974) 197–206, or appropriately supplemented or modified media.

According to German Offenlegungsschrift No. 1 642 749, when isolating the metal-free corrinoids a light intensity of 107.6 lux should not be exceeded. Since the process of the invention is directed to extra-cellular metal-free corrinoids that are exposed to light, in that process the light intensity used for the illumination is less than the light intensity of, for example, 2000 to 4000, especially 3000, lux conventionally used in the cultivation of phototrophic micro-organisms for obtaining intra-cellular metal-free corrinoids; compare, for example, with the known state of the art:

Koppenhagen & Pfiffner, J. Biol. Chem., 245 (1970) 5865–5867;

Koppenhagen & Pfiffner, J. Biol. Chem., 246 (1971) 3075–3077;

Koppenhagen, Dechema Grundkursus Biotechnologie, (1977) 75–92;

Toohey, Proc. Nat. Sci., 54 (1965) 934–942; and

Toohey, Fed. Proc., (1966) 1628–1632.

Surprisingly, in the process according to the invention it is possible, however, first of all to illuminate the culture with the light intensity of, for example, 2000 to 4000, especially 3000, lux, customary in the cultivation of phototrophic micro-organisms for obtaining intra-cellular metal-free corrinoids, and thereafter to illuminate the culture with a light intensity that is not so great in comparison. This embodiment of the process makes use of the fact that at the start of the growth phase hardly any metal-free corrinoids are secreted into the culture medium. A light intensity reduced by 50 to 90%, and especially by 60 to 80%, can be used, for example a light intensity of 1500 lux or less, 1000 lux or less or 500 lux or less.

If it is desired to reduce the light intensity only during the cultivation, the light intensity may advantageously be reduced when the optical density at 660 nm has reached a value in the range of from 2 to 4, especially in the range of from 2.5 to 3.

According to German Offenlegungsschrift No. 1 642 749, a pH of more than 7 should be avoided when isolating metal-free corrinoids. Although the process according to the invention is directed to the production of extra-cellular metal-free corrinoids, it has unexpectedly been discovered that operation can be carried out very well with the precultures and production cultures in a neutral or weakly alkaline range. According to one embodiment of the process, the pH is not re-adjusted when it changes and according to a different embodiment of the process the pH can be regulated to be in the range of from 7.5 to 9.0 and especially in the range of from 7.5 to 8.5.

By means of the process of the invention, the yield of metal-free corrinoids can be increased sixty-fold; thus, for example, for *Rhodopseudomonas sphaeroides* more than 5 mg/liter have already been obtained and for *Rhodopseudomonas capsulata* more than 1.5 mg/liter have been obtained.

The invention is explained in greater detail below by way of an Example.

CULTURE MEDIUM AND GROWTH CONDITIONS

The parent cultures were kept as liquid cultures in a chemically defined mineral medium prepared according to Pfennig (Arch. Mikrobiol., 100 (1974) 197–206), to which yeast extract (from Difco; 0.1% weight/volume) and disodium succinate (0.1% weight/volume) had been added. Sodium thiosulphate was left out. Sequential cultures were prepared every month from the parent cultures and incubated for 48 hours under light at 27° C.; they were stored at 4° C.

To produce the extra-cellular corrinoids, a modified Lascelles medium was used containing per liter of final volume, the following constituents:
5.38 g DL-malic acid;
500 mg potassium dihydrogen phosphate;
500 mg dipotassium hydrogen phosphate;
800 mg diammonium hydrogen phosphate;
200 mg magnesium sulphate.$7H_2O$;
40 mg calcium chloride;
2.86 mg boric acid;
1.81 mg manganese dichloride.$4H_2O$;
0.079 mg copper sulphate.$5H_2O$;
0.176 mg $H_2MoO_4.5H_2O$;
0.023 mg $NH_4VO_3$;
1 mg nicotinic acid;
1 mg thiamine hydrochloride; and
10 μg biotin.
The pH was adjusted to 6.8 with 2N NaOH.

To deplete the parent cultures of Fe and Co, precultures (or sequential cultures) were prepared 4 to 9 times in the said medium. Cultivation was carried out in 1 liter capacity flasks (Pyrex) having screw-type closures and filled completely in order to exclude air. The flasks were placed in a water bath that was maintained at a temperature of 27° C. The illumination was carried out with three reflector lamps (100 W), which were so positioned that they provided a uniform light intensity of 3000 lux at the inlet window of the water bath. In each flask the inoculate was 10%. The last stage of the depletion series served as the inoculum for 10-liter production cultures which grew under continuous illumination at 22° C. with no adjustment of the pH. When the cultures had reached an optical density of 3.0 at 660 nm, the initial light intensity of 3000 lux was reduced to 1000 and 600 lux. The cultures were allowed to grow for a total of 300 hours. After this time both strains (DSM 155 and 158) had reached the stationary phase (optical density 6.2 to 6.6), at which no further enrichment of extra-cellular corrinoids was observed. The pH had risen to a value in the range from 8.2 to 8.6.

Further production cultures were allowed to grow in a 350 liter tube photoreactor, which had been specially constructed for large-scale cultivation of phototrophic micro-organisms; see Koppenhagen, Dechema Grundkursus Biotechnologie, (1977) 75–92.

ISOLATION WITH *Rhodopseudomas sphaeroides*

After separating the cells by centrifugation, the reddish-brown supernatant liquid (which showed a strong reddish-orange fluorescence under ultra-violet light) was set to pH 3. Metal-free corrinoids together with large quantities of porphyrins and other hydrophobic compounds were absorbed on Amerberlite (XAD-2; 100 to 200 μm). The resin was washed until neutral; the corrinoids and the partially entrained porphyrins were eluted with tert.-butyl alcohol (20%). The butanol was removed under reduced pressure; the aqueous residue was introduced into a column charged with DEAE cellulose in the acetate form. Riboflavins and other yellow products, that were not characterised further, were quickly eluted with water, the porphyrins and the metal-free corrinoids being retained quantitatively at the top of the column. The corrinoids were separated from the mass of porphyrins by eluting with 0.5N acetic acid. The acidic eluate was transferred to a small XAD-2 bed (50 to 100 μm) from which the corrinoids were eluted with tert.-butyl alcohol (10%). The concentrated eluate was then again chromatographed on DEAE cellulose in the acetate form. The elution with aqueous acetic acid (1%) yielded four fractions of metal-free corrinoids with a total yield of 3.5 mg/liter of culture filtrate.

Details of the fractions obtained are as follows:
fraction 1: red pentacarboxylic acid;
fraction 2: yellow pentacarboxylic acid;
fraction 3: red hexacarboxylic acid; and
fraction 4: yellow hexacarboxylic acid.

The two red carboxylic acids were crystallised from aqueous solution as thin orange needles; main bands $\lambda_{max}$: 524, 498 and 329 nm; $\epsilon \times 10^{-3}$: 20.14, 18.64 and 48.37. The absorption spectra of the yellow fractions corresponded very significantly to those that were found for the yellow conversion products of the red decobalto corrinoids after treating with alkali (Toohey in Proc. Nat. Sci., 54 (1965) 934–942 and Fed. Proc., 25 (1966) 1628–1632); main absorption $\lambda_{max}$: 480, 462 (shoulder) and 290 nm; $\epsilon \times 10^{-3}$: 24.68, 23.58 and 39.72.

ISOLATION WITH *Rhodopseudomonas capsulata*

The method of isolating extra-cellular metal-free corrinoids was the same as that with *Rhodopseudomonas sphaeroides*. In addition to the hexa- and pentacarboxylic acids, this micro-organism yielded also tetra, tri-, di- and monocarboxylic acids and several neutral and basic products. After adsorption on an XAD-2 column and elution, the acid corrinoids were retained on DEAE cellulose in the acetate form and fractionated by elution with aqueous acetic acid (1%). The aqueous eluate contained the neutral and basic corrinoids which were separated off. The total yield of extracellular corrinoids was 0.4 mg/liter of culture filtrate.

We claim:

1. A process for obtaining metal-free corrinoids consisting of inoculating a culture media free of added compounds of metals of the VIIIth group of the Periodic Table with from 5% to 25% of a parent culture of a strain of Rhodpseudomas, cultivating under illumination, repeating the steps of inoculating and cultivating employing a fresh culture media free of added compounds of the VIIIth group of the Periodic Table and said illumination employing from 5% to 25% of the culture from the sequentially next preceding stage as an inoculum in each subsequent stage, for a series of several pre-production culture stages, inoculating a fresh culture media free of added compounds of metals of the VIIIth group of the Periodic Table with from 5% to 25% of the sequentially next preceding culture for the last time, cultivating under illumination, separating the microorganism from the culture media of the last culture stage and isolating metal-free corrinoids from the culture media of the last culture stage.

2. The process of claim 1 wherein, as said strain of Rhodopseudomonas, a strain selected from the group consisting of *Rhodopseudomonas sphaeroides*, *Rhodopseudomonas capsulata*, and *Rhodopseudomonas pallustris*, is employed.

3. The process of claim 1 or 2 wherein as inoculum for said last culture stage, a sequentially next preceding culture is employed wherein an extra-cellular concentration of at least 0.1 mg of metal-free corrinoids per liter can be obtained.

4. The process of claim 3 wherein said extra-cellular concentration is at least 0.5 mg of metal-free corrinoids per liter.

5. The process of claim 3 wherein said extra-cellular concentration is at least 1 mg of metal-free corrinoids per liter.

6. The process of claim 1 or 2 wherein said illumination is with a light intensity that is less than from 2,000 to 4,000 lux customary in the cultivation of phototrophic microorganisms for obtaining intracellular metal-free corrinoids.

7. The process of claim 1 or 2 wherein said illumination is first with the light intensity of from 2,000 to 4,000 lux customary in the cultivation of phototrophic microorganisms for obtaining intracellular metal-free corrinoids and thereafter when the optical density at 660 nm has reached a value in the range of from 2 to 4, with a reduced light intensity.

8. The process of claim 3 wherein said illumination is first with the light intensity of from 2,000 to 4,000 lux customary in the cultivation of phototrophic microorganisms for obtaining intracellular metal-free corrinoids and thereafter when the optical density at 660 nm has reached a value in the range of from 2 to 4, with a reduced light intensity.

9. The process of claim 6 wherein said reduced light intensity is from 50% to 90% of the light intensity of from 2,000 to 4,000 lux customary in the cultivation of phototropic microorganisms for obtaining intracellular metal-free corrinoids.

10. The process of claim 7 wherein said reduced light intensity is from 50% to 90% of the light intensity of from 2,000 to 4,000 lux customary in the cultivation of phototropic microorganisms for obtaining intracellular metal-free corrinoids.

11. The process of claim 8 wherein said reduced light intensity is from 50% to 90% of the light intensity of from 2,000 to 4,000 lux customary in the cultivation of phototropic microorganisms for obtaining intracellular metal-free corrinoids.

12. The process of claim 10 wherein said reduced light intensity is from 60% to 80%.

13. The process of claim 11 wherein said reduced light intensity is from 60% to 80%.

14. The process of claim 6 wherein said reduced light intensity is 1,500 lux or less.

15. The process of claim 7 wherein said reduced light intensity is 1,500 lux or less.

16. The process of claim 8 wherein said reduced light intensity is 1,500 lux or less.

17. The process of claim 14 or 15 or 16 wherein said reduced light intensity is 1,000 lux or less.

18. The process of claim 17 wherein said reduced light intensity is 500 lux or less.

19. The process of claim 7 wherein said optical density is in the range of 2.5 to 3.

20. The process of claim 8 wherein said optical density is in the range of 2.5 to 3.

21. The process of claim 1 or 2 wherein the pH of the culture from which the metal-free corrinoids are obtained is not readjusted when it changes.

22. The process of claim 1 or 2 wherein the pH of the culture from which the metal-free corrinoids are obtained is regulated within the range of from 7.5 to 9.

23. The process of claim 22 wherein said pH is regulated within the range of from 7.5 to 8.5.

24. The process of claim 1 wherein from 4 to 9 of said pre-production culture stages are employed.

25. The process of claim 6 where said light intensity is more than 107.6 lux.

26. A process for obtaining metal-free corrinoids consisting of inoculating a culture media free of added compounds of metals of the VIIIth group of the Periodic Table with from 5% to 25% of a parent culture of a strain of Rhodopseudomonas selected from the group consisting of *Rhodopseudomonas sphaeroides*, *Rhodopseudomonas capsulata*, and *Rhodopseudomonas pallustris*, cultivating under illumination, where said illumination is first with the light intensity of from 2,000 to 4,000 lux customary in the cultivation of phototrophic microorganisms for obtaining intracellular metal-free corrinoids and, thereafter, when the optical density at 660 mm has reached a value in the range of from 2 to 4, with a reduced light intensity, repeating the steps of inoculating and cultivating employing a fresh culture media free of added compounds of the VIIIth group of the Periodic Table and said illumination employing from 5% to 25% of the culture from the sequentially next preceding stage as an inoculum in each subsequent stage, for a series of several pre-production culture stages, inoculating a fresh culture media free of added compounds of metals of the VIIIth group of the Periodic Table with from 5% to 25% of the sequentially next preceding culture for the last time, cultivating under said illumination, separating the microorganism from the culture media of the last culture stage and isolating metal-free corrinoids from the culture media of the last culture stage.

* * * * *